(12) United States Patent
Matsumoto et al.

(10) Patent No.: US 9,869,614 B2
(45) Date of Patent: Jan. 16, 2018

(54) SAMPLING APPARATUS AND SAMPLING METHOD

(71) Applicant: Iwatani Corporation, Osaka (JP)

(72) Inventors: Kazuto Matsumoto, Hyogo (JP); Shinichi Omoteda, Hyogo (JP); Ken Nishida, Hyogo (JP); Goichi Inoue, Hyogo (JP)

(73) Assignee: IWATANI CORPORATION, Osaka (JP)

( * ) Notice: Subject to any disclaimer, the term of this patent is extended or adjusted under 35 U.S.C. 154(b) by 0 days.

(21) Appl. No.: 15/617,497

(22) Filed: Jun. 8, 2017

(65) Prior Publication Data

US 2017/0268965 A1 Sep. 21, 2017

Related U.S. Application Data

(63) Continuation of application No. PCT/JP2015/085002, filed on Dec. 15, 2015.

(30) Foreign Application Priority Data

Dec. 15, 2014 (JP) ................................ 2014-253025

(51) Int. Cl.
*G01N 1/22* (2006.01)
*G01N 33/00* (2006.01)

(52) U.S. Cl.
CPC ....... *G01N 1/2226* (2013.01); *G01N 33/0016* (2013.01); *G01N 2001/2238* (2013.01)

(58) Field of Classification Search
CPC ............. G01N 1/2226; G01N 33/0016; G01N 2001/2238

(Continued)

(56) References Cited

U.S. PATENT DOCUMENTS 2,411,235 A * 11/1946 Smith .................. F17C 5/06
141/105
5,562,130 A * 10/1996 Peha ..................... B64G 1/402
137/205

(Continued)

FOREIGN PATENT DOCUMENTS

JP 7-294395 11/1995
JP 2000-171362 6/2000

(Continued)

OTHER PUBLICATIONS

International Search Report dated Mar. 22, 2016 in International (PCT) Application No. PCT/JP2015/085002.

*Primary Examiner* — Hezron E Williams
*Assistant Examiner* — Marrit Eyassu
(74) *Attorney, Agent, or Firm* — Wenderoth, Lind & Ponack, L.L.P.

(57) ABSTRACT

A sampling apparatus includes a pressure-reducing safety unit, which includes a device accommodation chamber that accommodates safety devices and a cylinder connection chamber, and a cylinder unit. The cylinder unit removably accommodates a cylinder, excluding an exposed portion where a front end portion of the cylinder, a mouthpiece, and a cylinder on-off valve are exposed, in an openable/closable casing. The exposed portion of the cylinder is formed so as to be insertable from the open surface portion of the cylinder connection chamber into the cylinder connection chamber, the mouthpiece of the cylinder and a hydrogen outlet of a supply pipe of the device accommodation chamber are connected by using a flexible hose, and thereby a sample of hydrogen gas is taken into the cylinder.

5 Claims, 10 Drawing Sheets

(58) Field of Classification Search
USPC .................................................... 73/863.86
See application file for complete search history.

(56) References Cited

U.S. PATENT DOCUMENTS

| | | | | |
|---|---|---|---|---|
| 6,786,245 | B1* | 9/2004 | Eichelberger | B60S 5/02 141/18 |
| 8,267,128 | B2* | 9/2012 | Stuhlbacher | F17C 5/06 141/20 |
| 2001/0029979 | A1* | 10/2001 | Zheng | F17C 5/02 137/240 |
| 2003/0209282 | A1 | 11/2003 | Satou et al. | |
| 2004/0118476 | A1* | 6/2004 | Borck | F17C 5/06 141/4 |

FOREIGN PATENT DOCUMENTS

| | | |
|---|---|---|
| JP | 2003-57155 | 2/2003 |
| JP | 2006-59745 | 3/2006 |
| JP | 2006-322790 | 11/2006 |
| JP | 2008-39440 | 2/2008 |

\* cited by examiner

SAMPLING APPARATUS AND SAMPLING METHOD

CROSS REFERENCE TO RELATED APPLICATIONS

This application is a continuation of International Application PCT/JP2015/085002 filed on Dec. 15, 2015, which claims benefit of Japanese patent application JP2014-253025 filed on Dec. 15, 2014, both of which are incorporated herein by reference in their entireties.

TECHNICAL FIELD

The present invention relates to a sampling apparatus and a sampling method for analyzing impurities in fuel hydrogen gas that is supplied as a fuel of a fuel cell automobile or the like at a hydrogen station or the like. In particular, the present invention relates to a technology for an apparatus that includes a pressure-reducing safety unit and a cylinder unit for taking a sample of hydrogen gas to a cylinder from a storage container of fuel hydrogen gas for a fuel cell and that has safety and portability and a method using the apparatus.

BACKGROUND ART

In recent years, there is a global trend towards building a low-carbon society for preventing global warming, as part of global environmental protection. Also in Japan, projects to increase the number of fuel cell automobiles and to develop a hydrogen supply infrastructure are carried out by the government and the private sector. Not only fuel cell automobiles, but also trains, motorcycles, and forklift trucks that use fuel cells, and automobiles and other vehicles that directly use hydrogen as a fuel (hereinafter, referred to as "hydrogen vehicles") are attracting attention.

Therefore, as a hydrogen supply infrastructure, building of hydrogen stations is planned and promoted at a rapid pace.

Regarding fuel hydrogen gas that is supplied to a hydrogen vehicle at a hydrogen station or the like, if the hydrogen gas includes impurities, such as carbon monoxide and hydrogen sulfide, deterioration of the performance of a catalyst of a fuel cell occurs. Therefore, there are regulations on maximum permissible concentrations of various impurities.

Accordingly, it is necessary to identify and quantify a plurality of impurities included in fuel hydrogen gas that is supplied to a hydrogen vehicle at a hydrogen station or the like and to check that the concentrations of various impurities in the hydrogen gas are less than or equal to the maximum permissible concentrations. Moreover, it is necessary to periodically perform more precise analysis of the impurities.

However, because hydrogen stations have been built recently at a rapid pace, an apparatus or a method suitable for sampling hydrogen gas supplied at a hydrogen station is not known.

Examples of a sampling apparatus or a sampling method known to date include a gas sampling vessel including a safety valve device (see, for example, Japanese Unexamined Patent Application Publication No. 2008-39440), a high-purity-gas sampler (see, for example, Japanese Unexamined Patent Application Publication No. 2000-171362), and a rapid gas sampler (see, for example, Japanese Unexamined Patent Application Publication No. 7-294395).

In the existing technologies described in Japanese Unexamined Patent Application Publication No. 2008-39440, Japanese Unexamined Patent Application Publication No. 2000-171362 and Japanese Unexamined Patent Application Publication No. 7-294395, it is not disclosed that high-pressure hydrogen gas having a pressure of 70 MPa, which is supplied at a hydrogen station, can be safely sampled.

SUMMARY OF INVENTION

The present invention, which addresses such a problem of existing technologies, aims to ensure safety by using a rupture disk and a safety valve, to prevent unnecessary discharge of the hydrogen gas, and to take samples of hydrogen gas from a plurality of hydrogen stations or the like to a plurality of cylinders by transporting one sampling apparatus.

A sampling apparatus of the present invention is a sampling apparatus comprising a pressure-reducing safety unit and a cylinder unit for taking a sample of hydrogen gas to a cylinder from a storage container of fuel hydrogen gas to be supplied to a hydrogen vehicle.

The pressure-reducing safety unit includes a device accommodation chamber that accommodates devices and a cylinder connection chamber in which a flexible hose for sampling is connectable to the cylinder.

The device accommodation chamber accommodates a supply pipe that introduces high-pressure hydrogen gas from the storage container, a safety pipe that discharges hydrogen gas in the supply pipe when a pressure of the hydrogen gas exceeds a set pressure, and a discharge pipe that discharges gas in a pipe extending from the supply pipe to the cylinder.

A hydrogen inlet from the storage container is disposed at one end of the supply pipe, a hydrogen outlet to the cylinder is disposed at the other end of the supply pipe, and the hydrogen outlet is located near a boundary between the device accommodation chamber and the cylinder connection chamber.

A pressure-reducing valve that reduces a pressure of the high-pressure hydrogen gas introduced from the hydrogen inlet and a flow control valve that adjusts a flow rate of the hydrogen gas whose pressure has been reduced by the pressure-reducing valve are disposed in the supply pipe.

The safety pipe and the discharge pipe, in which a discharge on-off valve is disposed, branch from a branching portion of the supply pipe between the pressure-reducing valve and the flow control valve.

A main valve, a rupture disk that opens the safety pipe at a first set pressure or higher, and a safety valve that opens at a second set pressure lower than the first set pressure and closes at a third set pressure lower than the second set pressure are disposed in the safety pipe in order from the branching portion of the supply pipe.

The cylinder connection chamber includes an open surface portion that opens toward the outside.

The cylinder unit removably accommodates the cylinder, excluding an exposed portion where a front end portion of the cylinder, a mouthpiece, and a cylinder on-off valve are exposed, in an openable/closable casing.

The exposed portion of the cylinder is formed so as to be insertable from the open surface portion of the cylinder connection chamber into the cylinder connection chamber, and the sample of hydrogen gas is taken into the cylinder by connecting the mouthpiece of the cylinder and the hydrogen outlet by using the flexible hose.

A sampling method of the present invention is a sampling method for taking a sample of hydrogen gas to a cylinder from a storage container of fuel hydrogen gas to be supplied to a hydrogen vehicle by using a sampling apparatus including a pressure-reducing safety unit and a cylinder unit.

The pressure-reducing safety unit includes a device accommodation chamber that accommodates devices and a cylinder connection chamber in which a flexible hose for sampling is connectable to the cylinder.

The device accommodation chamber accommodates a supply pipe that introduces high-pressure hydrogen gas from the storage container, a safety pipe that discharges hydrogen gas in the supply pipe when a pressure of the hydrogen gas exceeds a set pressure, and a discharge pipe that discharges gas in a pipe extending from the supply pipe to the cylinder.

A hydrogen inlet from the storage container is disposed at one end of the supply pipe, a hydrogen outlet to the cylinder is disposed at the other end of the supply pipe, and the hydrogen outlet is located near a boundary between the device accommodation chamber and the cylinder connection chamber.

A pressure-reducing valve that reduces a pressure of the high-pressure hydrogen gas introduced from the hydrogen inlet and a flow control valve that adjusts a flow rate of the hydrogen gas whose pressure has been reduced by the pressure-reducing valve are disposed in the supply pipe.

The safety pipe and the discharge pipe, in which a discharge on-off valve is disposed, branch from a branching portion of the supply pipe between the pressure-reducing valve and the flow control valve.

A main valve, a rupture disk that opens the safety pipe at a first set pressure or higher, and a safety valve that opens at a second set pressure lower than the first set pressure and closes at a third set pressure lower than the second set pressure are disposed in the safety pipe in order from the branching portion of the supply pipe.

The cylinder connection chamber includes an open surface portion that opens toward the outside.

The cylinder unit removably accommodates the cylinder, excluding an exposed portion where a front end portion of the cylinder, a mouthpiece, and a cylinder on-off valve are exposed, in an openable/closable casing.

The sampling method includes:

inserting the exposed portion of the cylinder into the cylinder connection chamber from the open surface portion of the cylinder connection chamber, connecting the mouthpiece of the cylinder and the hydrogen outlet by using the flexible hose, and connecting the hydrogen inlet to a filling hole of the storage container;

filling an inside of the supply pipe, an inside of the flexible hose, and an inside of the discharge pipe with hydrogen gas by opening the flow control valve, subsequently stopping the filling by closing the flow control valve, discharging gas by opening the discharge on-off valve, and discharging residual hydrogen gas in the cylinder by opening the cylinder on-off valve; and starting filling an inside of the cylinder from the storage container by closing the discharge on-off valve and opening the flow control valve to take the sample of hydrogen gas into the cylinder.

The sampling apparatus or the sampling method of the present invention has an advantage effect in that if the inside of the supply pipe is excessively filled to have a pressure higher than equal to the first set pressure due to malfunctioning of the pressure-reducing valve, the rupture disk immediately opens the safety pipe and hydrogen gas is discharged through the safety valve to ensure safety, and, when the pressure in the safety pipe decreases to the third set pressure due to the discharge, the safety valve is closed to prevent unnecessary discharge of the hydrogen gas.

There is also an advantage effect in that the cylinder for a sample of hydrogen gas is replaceable, and, by transporting one sampling apparatus, it is possible to take samples of hydrogen gas to a plurality of cylinders from storage containers of fuel hydrogen gas, which is to be supplied to hydrogen vehicles, at a plurality of hydrogen stations.

Further, in the sampling apparatus of the present invention, the pressure-reducing safety unit includes four caster wheels at a bottom portion of a lower frame body and is portable, and the cylinder unit includes four caster wheels at a bottom portion and is portable.

Therefore, the sampling apparatus has an advantageous effect in that the pressure-reducing safety unit and the cylinder unit can be set and removed easily by moving these units when taking a sample of hydrogen gas from the storage container.

Further, in the sampling apparatus of the present invention, the casing of the cylinder unit has a horizontally-elongated rectangular-parallelepiped shape and includes a pair casings formed by dividing an upper surface at a center in a longitudinal direction, each of the pair of casings including a side surface and a divided upper surface and having an L-shaped vertical cross section perpendicular to the longitudinal direction; and a plurality of hinges are disposed at a lower end of the side surface of each of the pair of casings and a grip for opening/closing is disposed on the divided upper surface of each of the pair of casings, so that the pair of casings are openable/closable.

Therefore, the sampling apparatus has an advantageous effect in that the cylinder can be easily attached to or removed from the cylinder unit.

Further, in the sampling apparatus of the present invention, the cylinder unit includes a rotatable frame including an angular C-shaped frame body including a pair of frame members that are parallel to a longitudinal direction of the cylinder and a first handle that connects one end portions of the pair of frame members, a pair of wheels disposed at end portions of the frame body, a connection member that connects portions of the frame body near end portions, and a rotatable arm one end of which is attached so as to be rotatable with a center of the connection member as a fulcrum and the other end of which is attached so as to be rotatable with a center of a bottom frame of the cylinder unit in the longitudinal direction as a fulcrum, the rotatable frame allowing positions of the pair of wheels disposed on the frame body to be variable.

The bottom frame includes a first engagement portion and a second engagement portion that engage with the first handle when the rotatable frame is rotated.

When the rotatable frame is rotated and the first handle engages with the first engagement portion, the pair of wheels, whose positions are variable, are located near the other pair of wheels near a bottom portion of the cylinder.

When the rotatable frame is rotated and the first handle engages with the second engagement portion, the rotatable arm and the angular C-shaped frame body form a predetermined angle and one of the pairs of wheels and the other pair of wheels are positioned on the same plane so as to be separated by a predetermined distance and the cylinder unit is in an inclined state.

Therefore, the sampling apparatus has an advantageous effect in that the cylinder unit can be easily handled by changing the shape (position) of the cylinder unit.

DESCRIPTION OF EMBODIMENTS

Hereinafter, an embodiment of the present invention will be described in detail with reference to the drawings.

Figure 1:
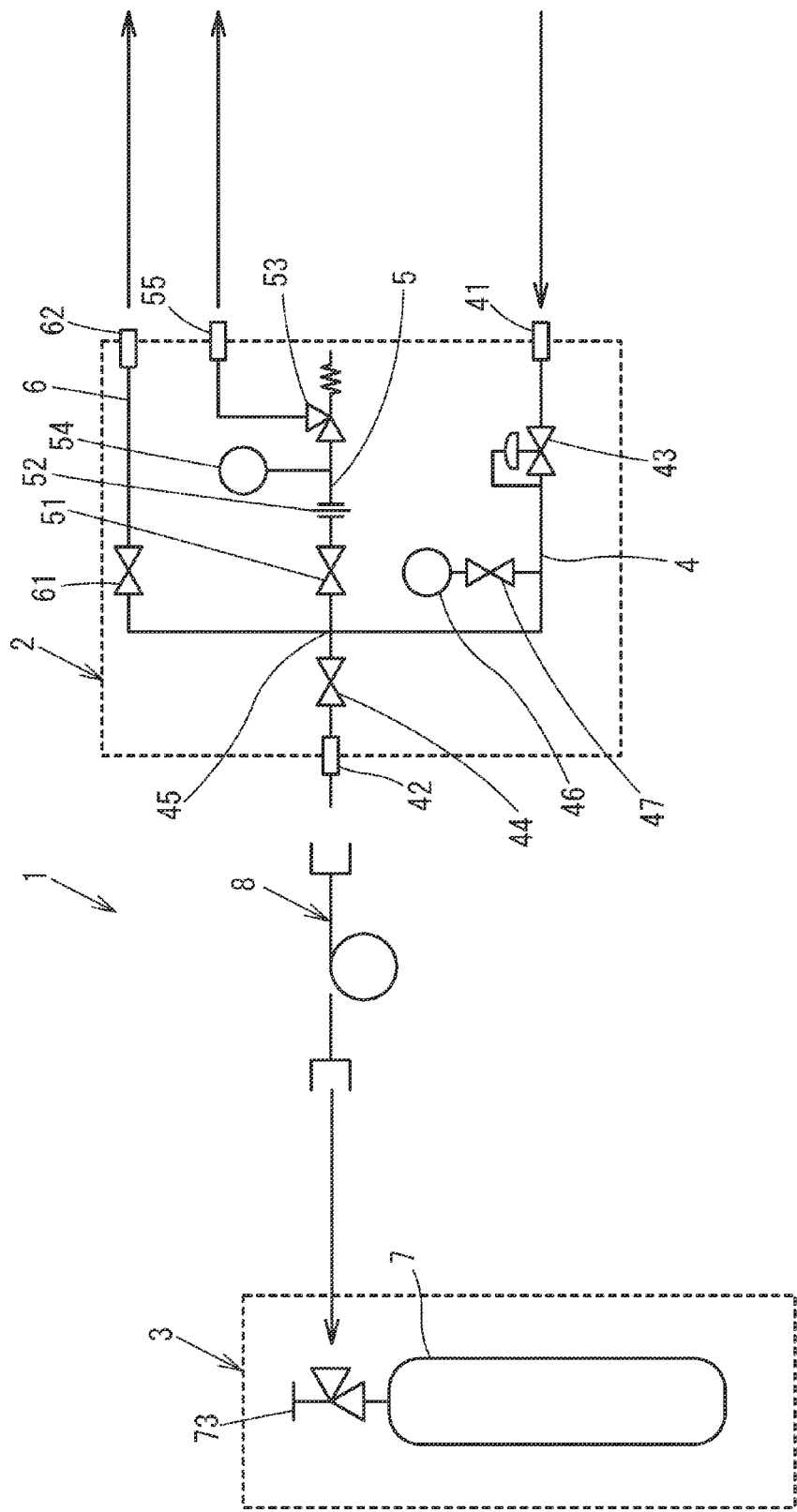
FIG. 1 illustrates pipes of a sampling apparatus according to an embodiment of the present invention.
Figure 2:
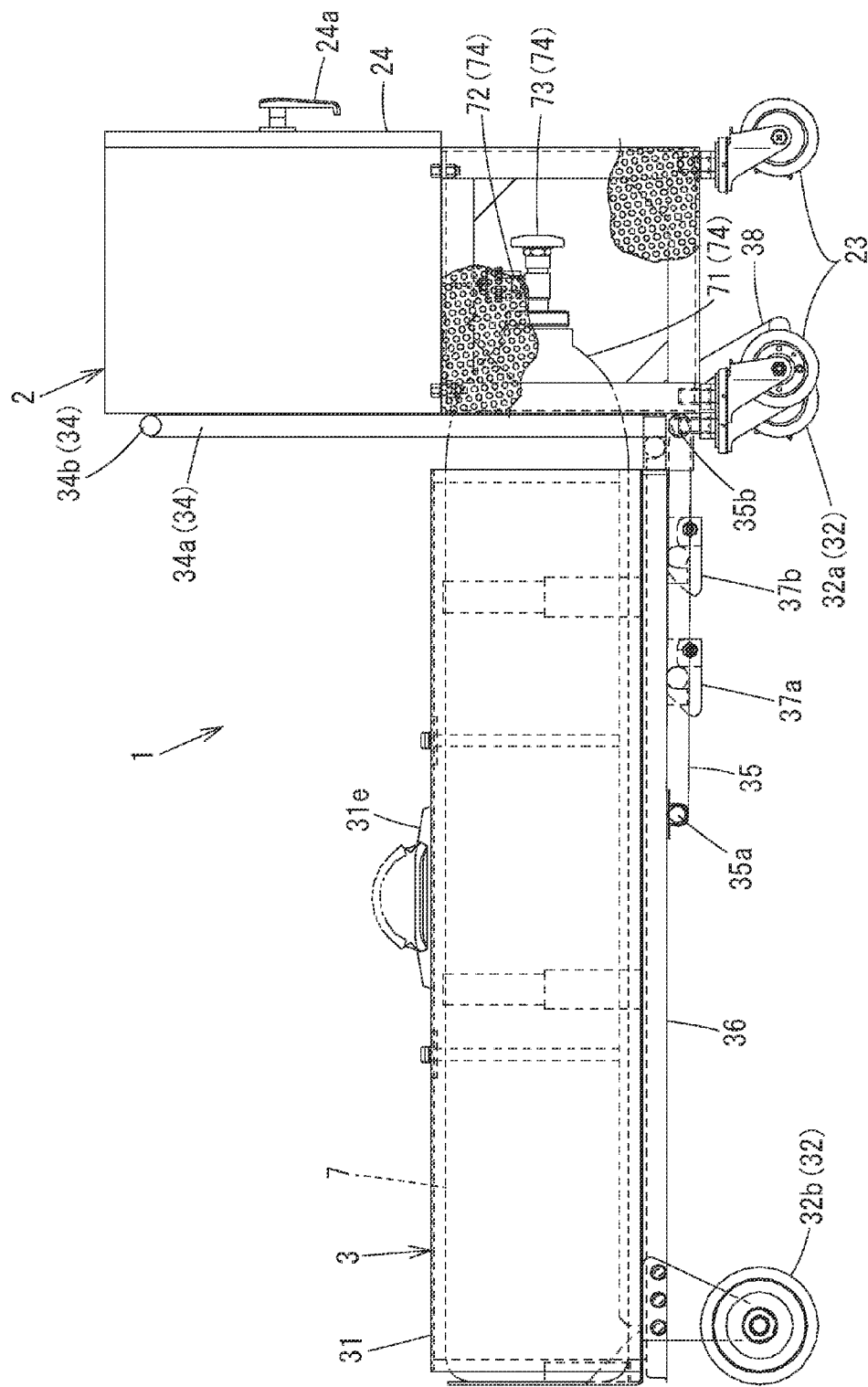
FIG. 2 is a front view of the sampling apparatus according to the embodiment of the present invention.
Figure 3:
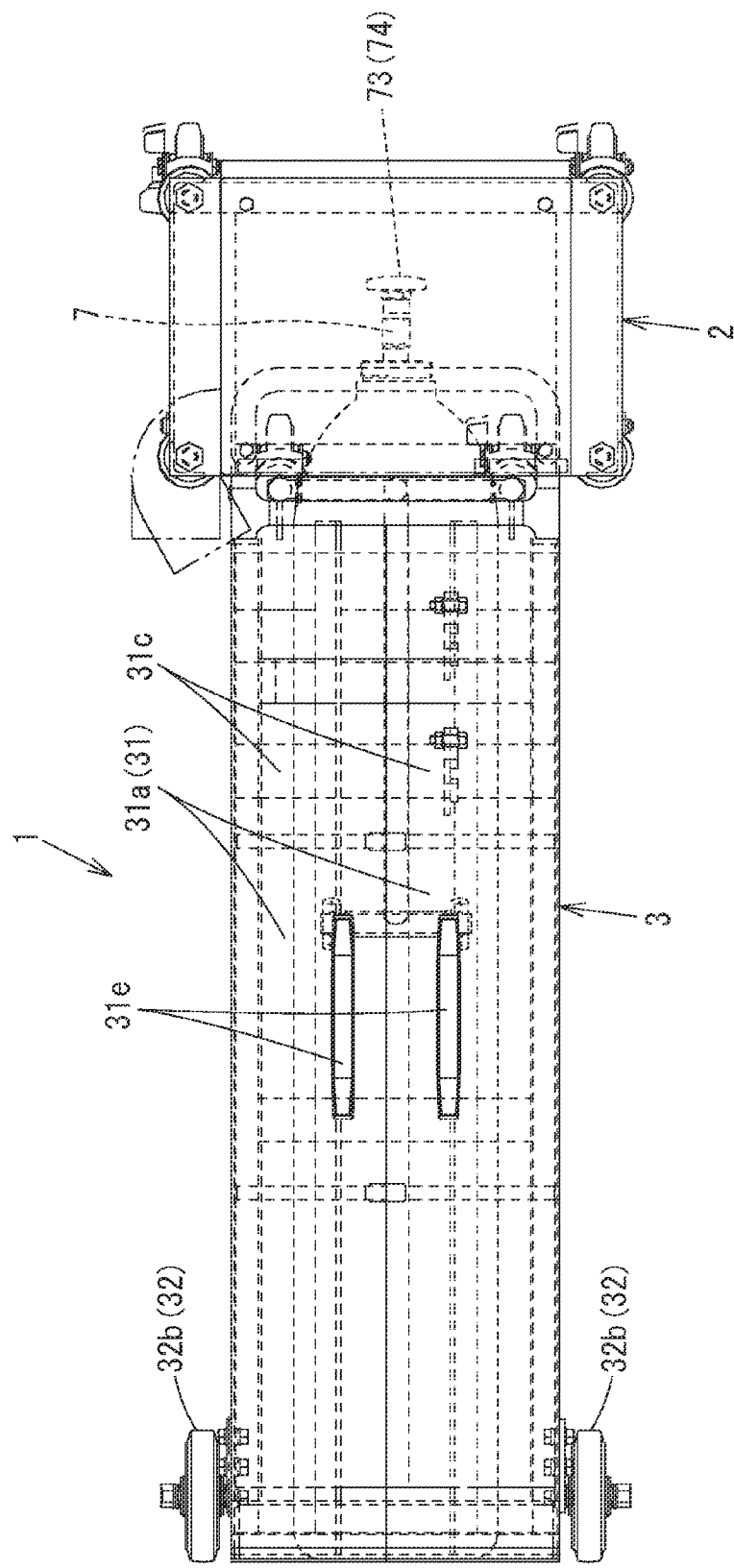
FIG. 3 is a plan view of FIG. 2.
Figure 4:
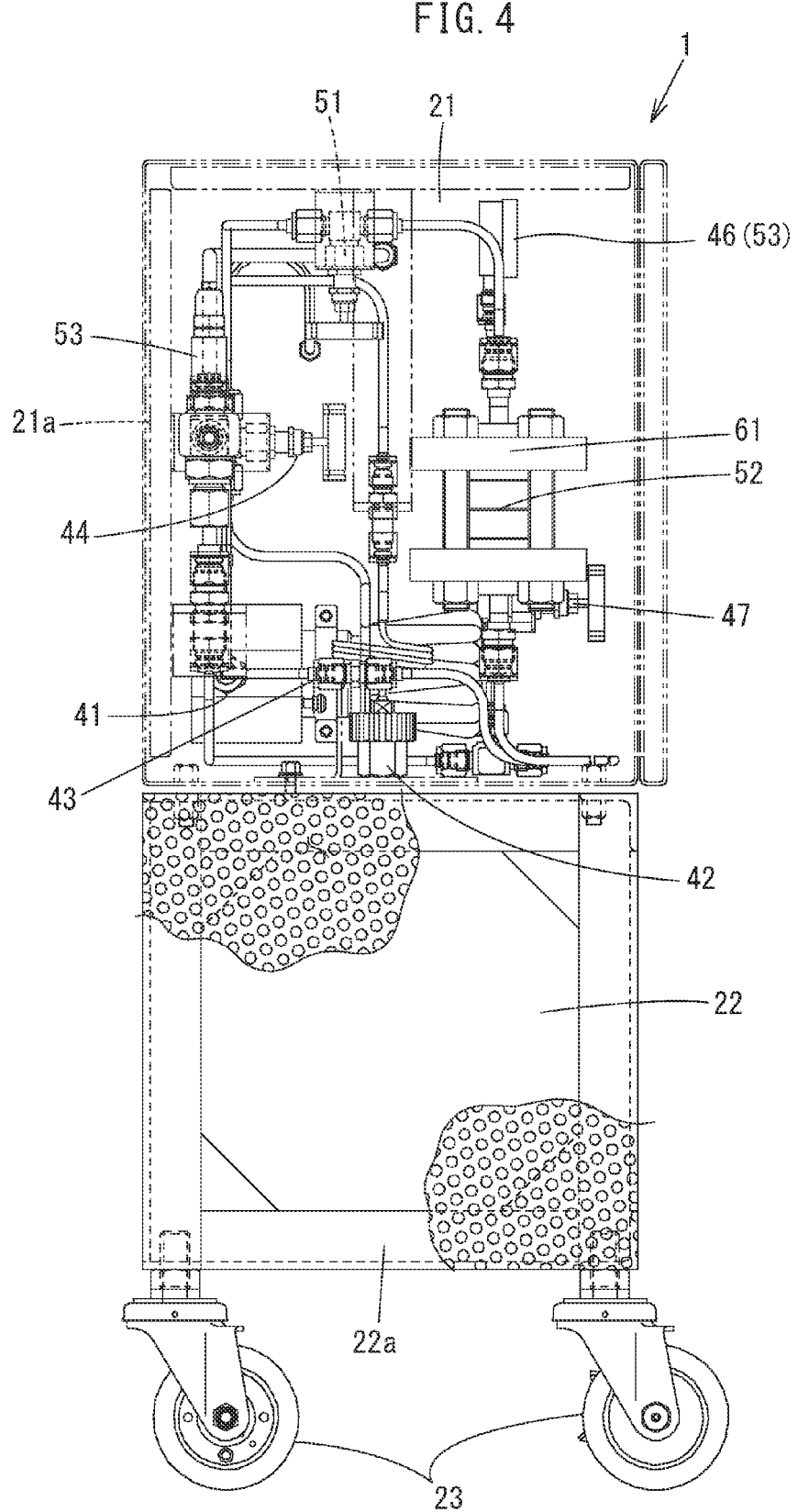
FIG. 4 is a front view illustrating devices of a pressure-reducing safety unit according to the embodiment of the present invention.
Figure 5:
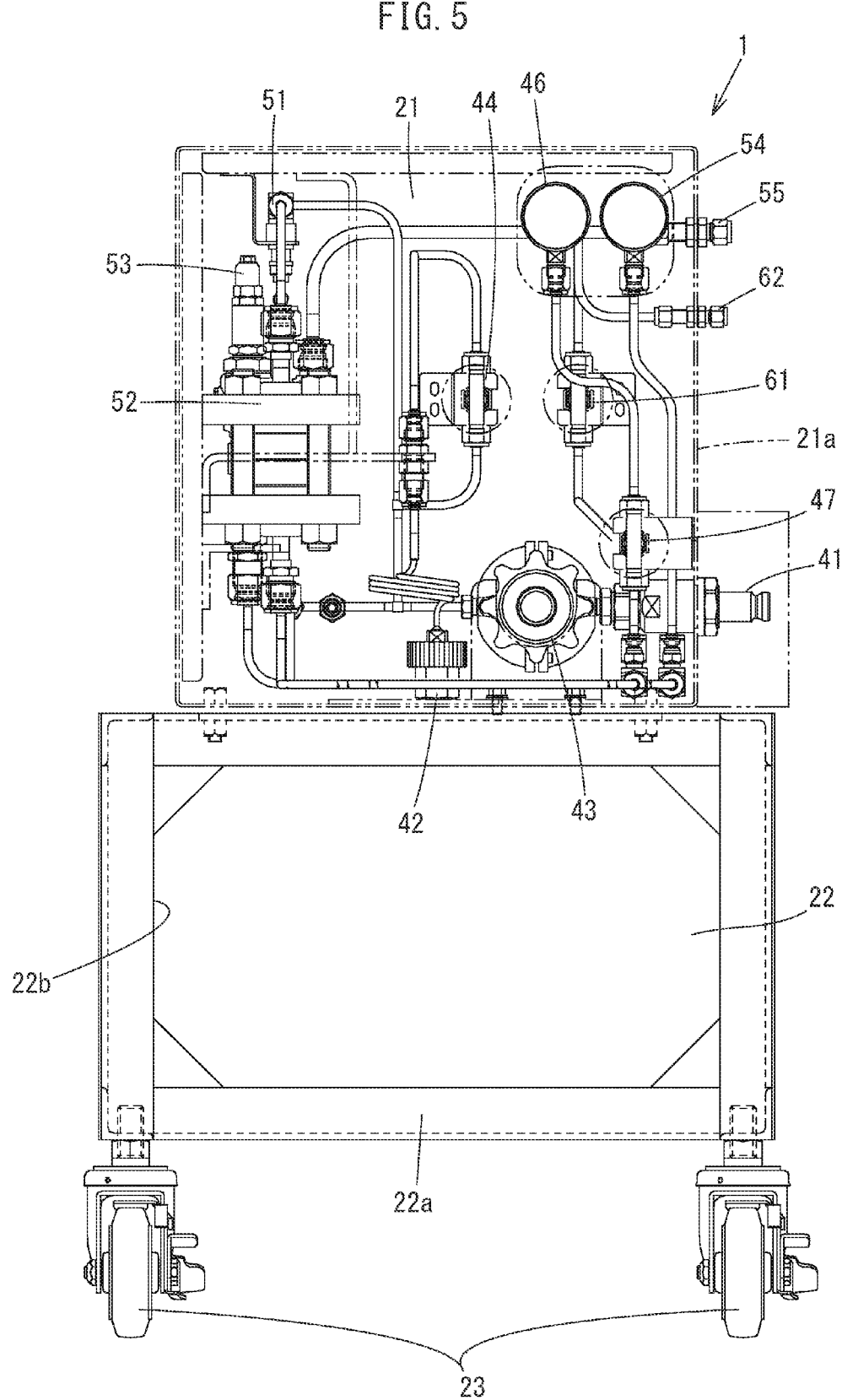
FIG. 5 is a side view of FIG. 4.
Figure 6:
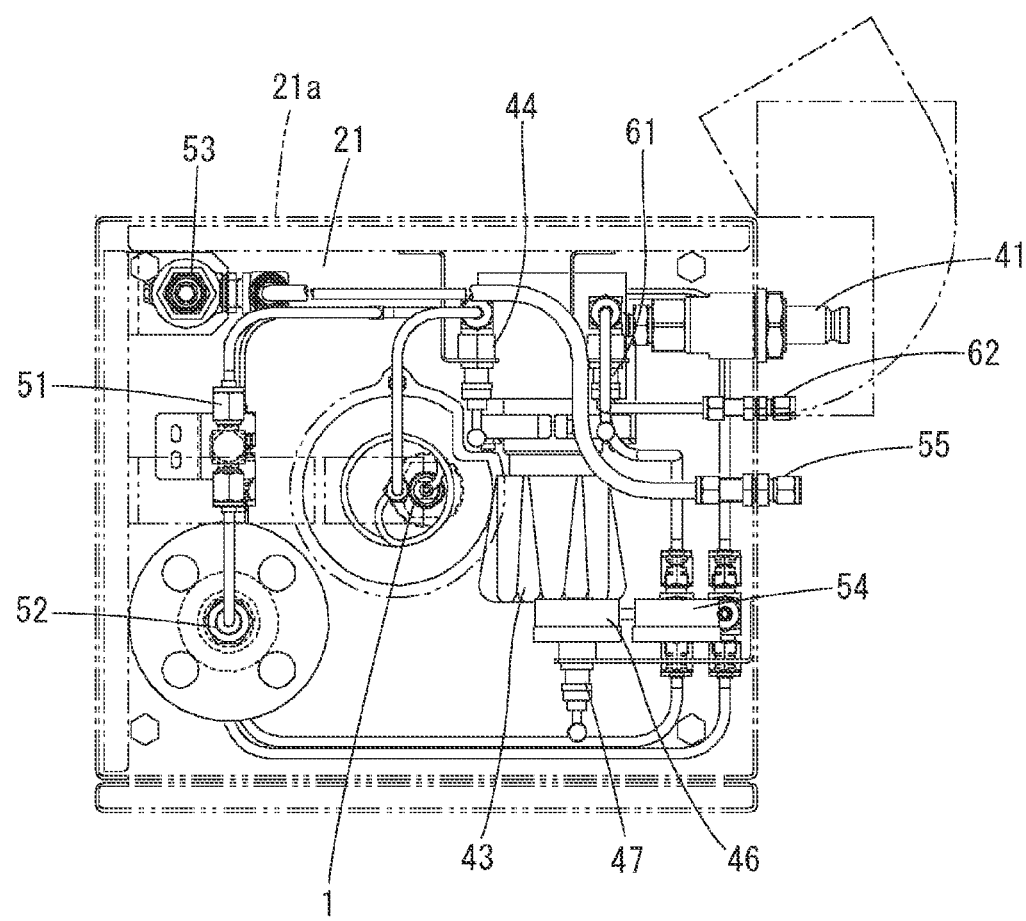
FIG. 6 is a plan view of FIG. 5.

FIGS. 2 and 3 illustrate a sampling apparatus according to the embodiment of the present invention, FIGS. 4 to 6 illustrate a pressure-reducing safety unit of the sampling apparatus according to the embodiment of the present invention, and FIGS. 7 to 10 illustrate a cylinder unit of the sampling apparatus according to the embodiment of the present invention.

Referring to FIGS. 1 to 10, a sampling apparatus according to an embodiment of the present invention will be described.

A sampling apparatus 1 includes a pressure-reducing safety unit 2 and a cylinder unit 3 for taking a sample of hydrogen gas to a cylinder 7 through a filling nozzle (not shown) that is used to supply fuel hydrogen gas from a storage container at a hydrogen station to a vehicle-mount container of a hydrogen vehicle.

It is necessary to identify and quantify a plurality of impurities included in fuel hydrogen gas that is supplied to a hydrogen vehicle at a hydrogen station or the like and to check that the concentrations of various impurities in the hydrogen gas are less than or equal to the maximum permissible concentrations. Moreover, it is necessary to periodically perform more precise analysis of the impurities. The cylinder 7 is a container for containing and conveying a sample of hydrogen gas that is used for the analysis of such impurities.

The pressure-reducing safety unit 2 includes an upper frame body 21a and a lower frame body 22a. A device accommodation chamber 21, which accommodates various devices, is formed in the upper frame body 21a. A cylinder connection chamber 22, in which a flexible hose 9 for taking a sample of hydrogen gas is to be connected to the cylinder 7, is formed in the lower frame body 22a.

The device accommodation chamber 21 accommodates a supply pipe 4, a safety pipe 5, and a discharge pipe 6. The supply pipe 4 introduces high-pressure hydrogen gas having a pressure of 70 MPa from a storage container of a fuel hydrogen gas, which is supplied to a hydrogen vehicle at a hydrogen station or the like. The safety pipe 5 discharges hydrogen gas in the supply pipe 4 when the pressure of the hydrogen gas exceeds a set pressure of, for example, 14.5 MPa. The discharge pipe 6 discharges gas in a pipe extending from the supply pipe 4 to the cylinder 7.

A hydrogen inlet 41 from the storage container is disposed at one end of the supply pipe 4. A hydrogen outlet 42 to the cylinder 7 is disposed at the other end of the supply pipe 4. The hydrogen outlet 42 is located near the boundary between the device accommodation chamber 21 and the cylinder connection chamber 22.

A pressure-reducing valve 43 and a flow control valve 44 are disposed in the supply pipe 4. The pressure-reducing valve 43 reduces the pressure of the high-pressure hydrogen gas, having a pressure of 70 MPa and introduced from the hydrogen inlet 41, to 14 MPa. The flow control valve 44 adjusts the flow rate of the hydrogen gas, whose pressure has been reduced by the pressure-reducing valve 43.

The safety pipe 5 and the discharge pipe 6, in which a discharge on-off valve 61 is disposed, branch from a branching portion 45 of the supply pipe 4 between the flow control valve 44 and the pressure-reducing valve 43.

A main valve 51, a rupture disk 52, and a safety valve 53 are disposed in the safety pipe 5 in order from the branching portion 45 of the supply pipe 4. The rupture disk 52 opens the safety pipe 5 at a first set pressure or higher. The safety valve 53 opens at a second set pressure lower than the first set pressure and closes at a pressure lower than the second set pressure.

Here, the specifications of the cylinder 7 are: type 47L (type 7), internal volume 47 L, diameter 232 mm, length 1320 mm, fill volume 7 m$^3$ (14.7 MPa). The first set pressure is set at 14.5 MPa so as to correspond to the specifications of the cylinder 7, in which the maximum use pressure is 14.7 MPa.

The second set pressure is set at 14.0 MPa and a third set pressure is set at 13.5 MPa so that, when the pressure in the safety pipe 5 becomes the first set pressure, the rupture disk 52 can immediately rupture to open the safety pipe 5 and hydrogen gas can be discharged through the safety valve 53 and thereby safety can be maintained.

When the pressure in the safety pipe 5 decreases to the third set pressure due to the discharge, the safety valve 53 automatically closes to prevent unnecessary discharge of hydrogen gas.

Moreover, because the rupture disk 52 and a pressure gauge 54 are provided, in contrast a case where only the safety valve 53 is provided, atmospheric components do not enter from the outside and, if a very small crack is formed in the rupture disk 52, the crack can be detected by using the pressure gauge 54. Therefore, negative influence on measurement of the concentrations of nitrogen and oxygen, which are items to be measured, in a sample can be more effectively prevented.

The upper frame body 21a is placed on the lower frame body 22a, and a bottom surface of the device accommodation chamber 21 and an upper surface of the cylinder connection chamber 22 are open.

The cylinder connection chamber 22 includes an open surface portion 22b, which is open, in a left side surface thereof.

The cylinder unit 3 removably accommodates the cylinder 7, excluding an exposed portion 74 where a front end portion 71 of the cylinder 7, a mouthpiece 72, and an on-off valve 73 are exposed, in a casing 31, including openable/closable casings 31a, in such a way that a cylindrical portion of the cylinder 7 is placed horizontally.

The exposed portion 74 of the cylinder 7 is insertable into the cylinder connection chamber 22 from the open surface portion 22b of the cylinder connection chamber 22 of the pressure-reducing safety unit 2. A sample of hydrogen gas is taken into the cylinder 7 by connecting the mouthpiece 72 of the cylinder 7 and the hydrogen outlet 42 of the pressure-reducing safety unit 2 by using a flexible hose 8.

The pressure-reducing safety unit 2 includes four caster wheels 23 on a bottom portion of the lower frame body 22a and is also portable. Thus, when taking a sample of hydrogen gas from the storage container, the pressure-reducing safety unit 2 can set and removed easily by moving the pressure-reducing safety unit 2.

As with the pressure-reducing safety unit 2, the cylinder unit 3 also includes four caster wheels 32 at a bottom portion thereof and is portable. Thus, when taking a sample of hydrogen gas from the storage container, the cylinder unit 3 can be set and removed easily by moving the cylinder unit 3.

Moreover, the casing 31 of the cylinder unit 3 has a horizontally-elongated rectangular-parallelepiped shape and includes the pair of casings 31a formed by dividing an upper surface at the center in the longitudinal direction. Each of the pair of casings 31a includes a side surface 31b and a divided upper surface 31c and has an L-shaped vertical cross section perpendicular to the longitudinal direction. A plurality of hinges 31d are disposed at a lower end of the side surface 31b of each of the pair of casings 31a and a grip 31e for opening/closing is disposed on the divided upper surface 31c of each of the pair of casings 31a. Thus, the pair of casings 31a are openable/closable. Therefore, the cylinder 7 can be easily attached to or removed from the cylinder unit 3.

The cylinder unit 3 includes a pair of arc-shaped support members 33, which support the cylindrical portion of the cylinder 7, in the casing 31. A cushioning member (not shown) is wound around the cylindrical portion of the cylinder 7, and the cylinder 7 is removably fixed to the support members 33 by using a pair of bands (not shown). By structuring the cylinder unit 3 in this way, the cylinder 7 can be protected against a shock during transportation and the like.

The cylinder unit 3 can be easily handled by changing its shape (position). The structure for this will be described below.

A rotatable frame 37 includes a frame body 34, a pair of wheels 32a, a connection member (not shown), and a rotatable arm 35. The frame body 34 is angular C-shaped and includes a pair of frame members 34a, which are parallel to the longitudinal direction of the cylinder 7, and a first handle 34b, which connects one end portions of the pair of frame members 34a. The pair of wheels 32a are disposed at end portions of the frame body 34. The connection member c connects portions of the frame body 34 near end portions. One end of the rotatable arm 35 is attached so as to be rotatable with the center of the connection member as a first fulcrum 35b, and the other end of the rotatable arm 35 is attached so as to be rotatable with the center of a bottom frame 36 of the cylinder unit 3 in the longitudinal direction as a second fulcrum 35a. The rotatable frame 37 allows the positions of the pair of wheels 32a disposed on the frame body 34 to be variable.

The bottom frame 36 includes a first engagement portion 37a and a second engagement portion 37b, which engage with the first handle 34b when the rotatable frame 37 is rotated.

Figure 7:
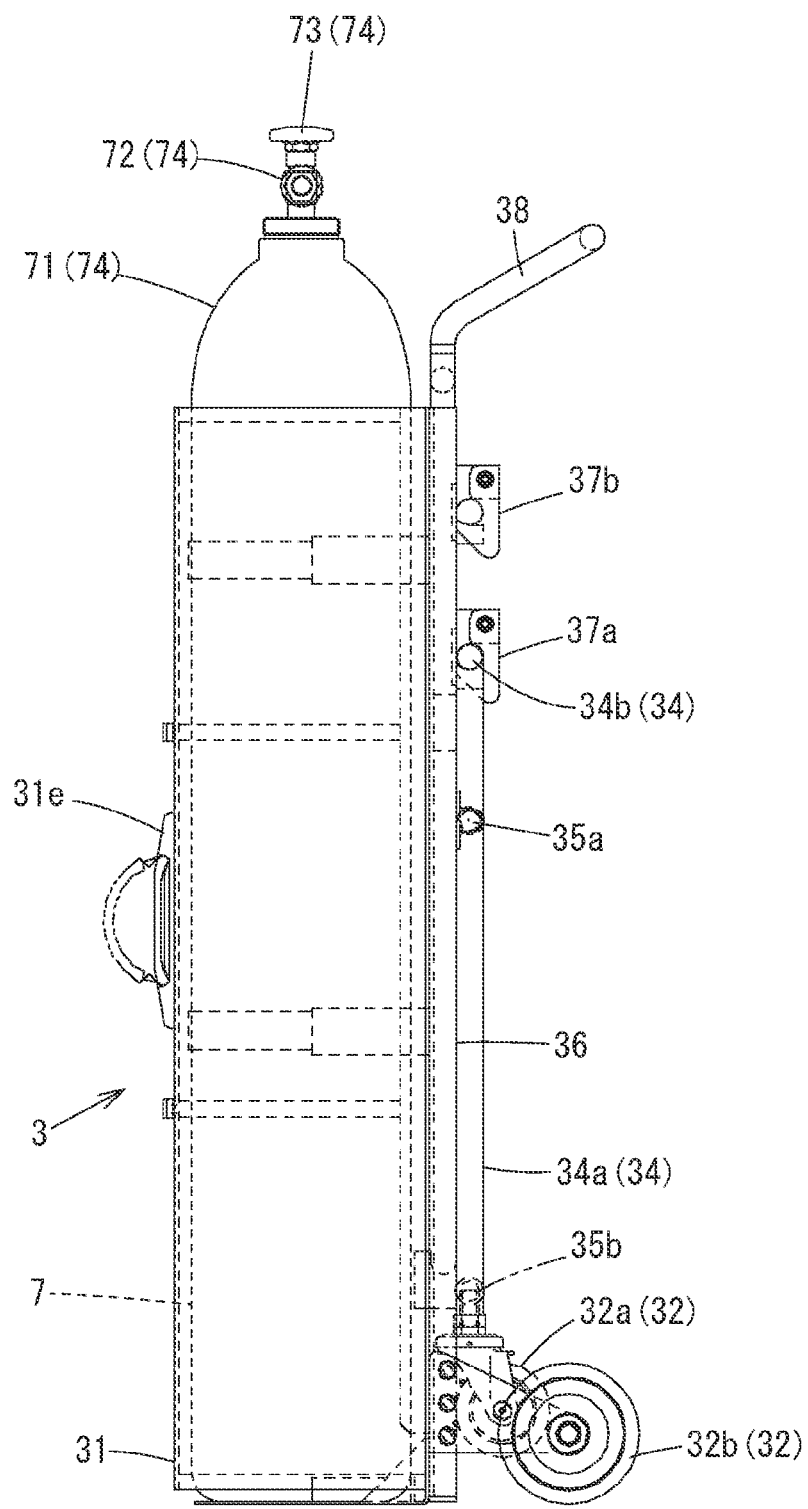
FIG. 7 is a front view illustrating a cylinder unit according to the embodiment of the present invention in an inverted state.
Figure 8:
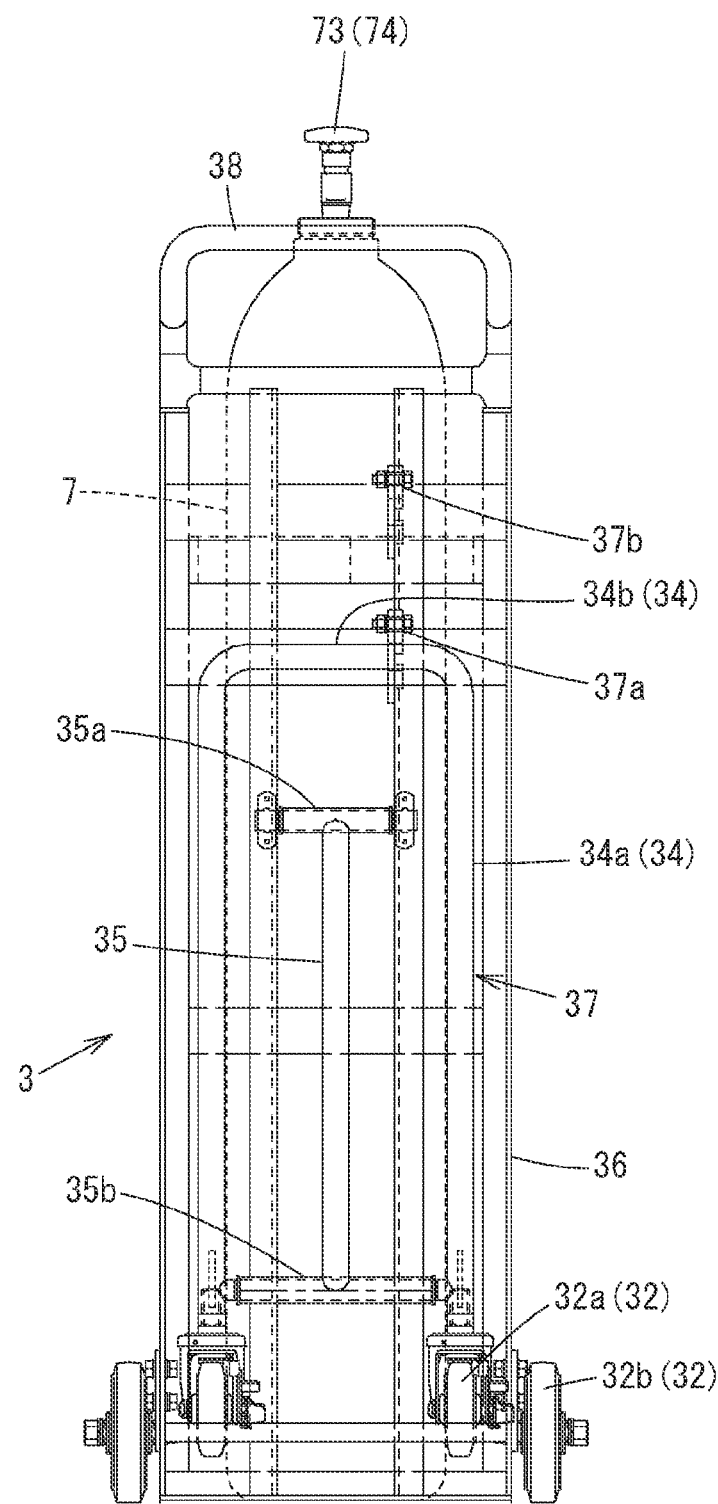
FIG. 8 is a right side view of FIG. 7.
Figure 9:
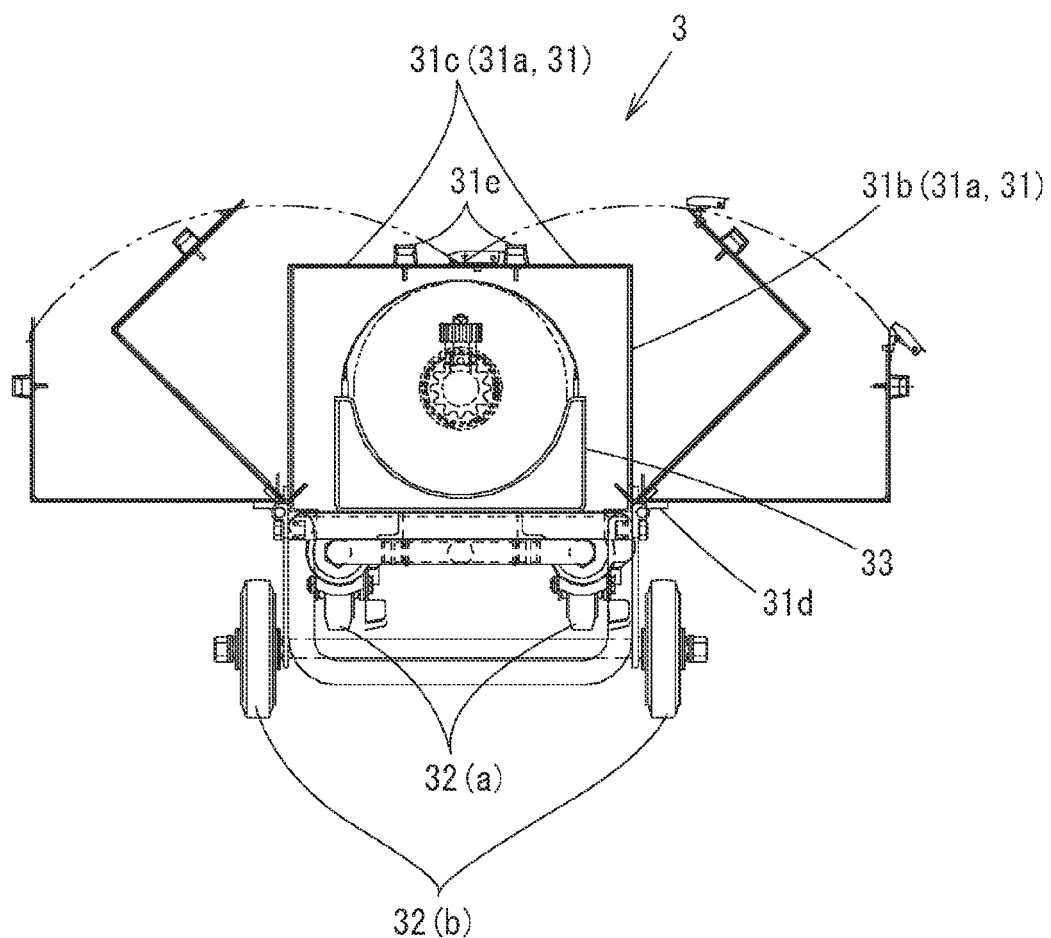
FIG. 9 is a plan view of FIG. 8 illustrating a casing in an open state or in a closed state.

As illustrated in FIGS. 7 to 9, when the rotatable frame 37 is rotated and the first handle 34b engages with the first engagement portion 37a, the pair of wheels 32a, whose positions are variable, are located near the other pair of wheels 32b near the bottom portion of the cylinder 7.

Figure 10:
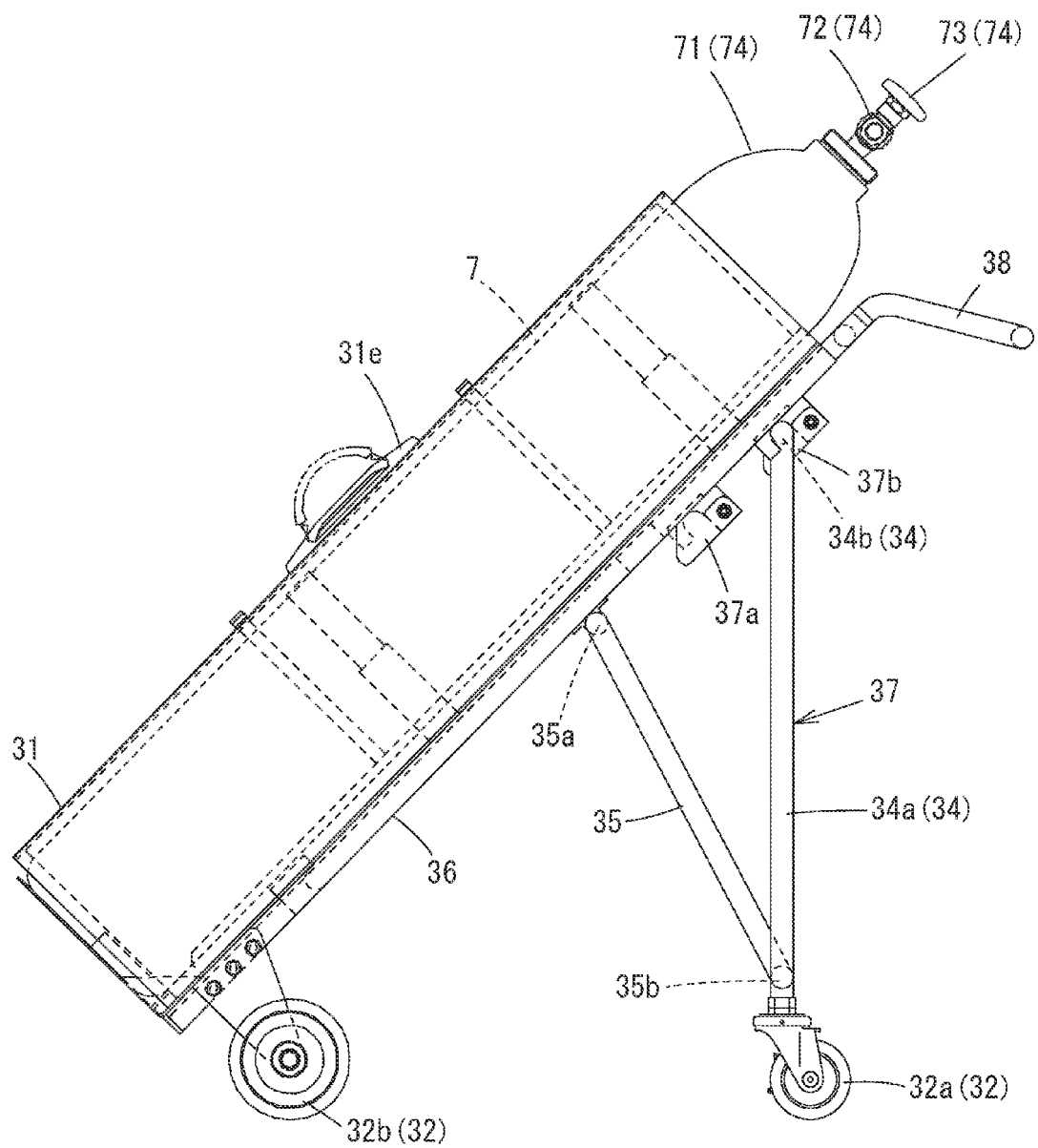
FIG. 10 is a front view illustrating the cylinder unit according to the embodiment of the present invention in an inclined state.

As illustrated in FIG. 10, when the rotatable frame 37 is rotated and the first handle 34b engages with the second engagement portion 37b, the rotatable arm 35 and the angular C-shaped frame body 34 form a predetermined angle of, for example, 30 degrees; and one of the pairs of wheels 32a and the other pair of wheels 32b are positioned on the same plane so as to be separated by a predetermined distance and the cylinder unit 3 is inclined by, for example, 50 degrees.

As illustrated in FIG. 7, the bottom frame 36 of the cylinder unit 3 includes a second handle 38 below the exposed portion 74 of the cylinder 7. The second handle 38 is inclined forward and downward and is angular C-shaped in plan view.

When causing the cylinder unit 3 to be in an inverted position as shown in FIG. 7, the cylinder unit 3 is raised by holding the second handle 38 so as to move the exposed portion 74 of the cylinder 7 upward, and the rotatable frame 37 is rotated so that the first handle 34b engages with the first engagement portion 37a as described above. Thus, the pair of wheels 32a, whose positions are variable, are located near the other pair of wheels 32b near the bottom portion of the cylinder 7.

The numeral 24 represents a door of the device accommodation chamber 21 including a door handle 24a, the numeral 46 represents a pressure gauge that measures the pressure in the supply pipe 4 between the pressure-reducing valve 43 and the flow control valve 44, the numeral 47 represents a pressure gauge main valve, the numeral 54 represents the pressure gauge that measures the pressure in the safety pipe 5 between the rupture disk 52 and the safety valve 53, the numeral 55 represents an outlet of the safety pipe 5, and the numeral 62 represents a discharge port of the discharge pipe 6. The outlet 55 of the safety pipe 5 and the discharge port 62 of the discharge pipe 6 are connected to a discharge line of a hydrogen station (not shown).

Next, a sampling method for taking a sample of hydrogen gas to the cylinder 7 from a storage container of fuel hydrogen gas to be supplied to a hydrogen vehicle, by using the sampling apparatus 1 having the aforementioned structure will be described.

First, the cylinder 7 is set in the cylinder unit 3.

Preferably, a cylinder containing residual hydrogen gas is used as the cylinder 7.

Preferably, the pressure of the residual hydrogen gas is higher than the atmospheric pressure and lower than the first set pressure, at which the safety pipe 5 is opened. More preferably, the pressure of the residual hydrogen gas is 0.3 MPa or higher and 1 MPa or lower so that entry of atmospheric components can be prevented and unnecessary discharge of hydrogen gas can be reduced.

Next, by moving the cylinder unit 3, as illustrated in FIGS. 2 and 3, the exposed portion 74 of the cylinder 7 is inserted into the cylinder connection chamber 22 from the open surface portion 22b of the cylinder connection chamber 22 of the pressure-reducing safety unit 2.

Next, the mouthpiece 72 of the cylinder 7 and the hydrogen outlet 42 are connected by using the flexible hose 8, and the hydrogen inlet 41 is connected to the filling hole of the storage container.

The cylinder on-off valve 73 and the flow control valve 44 are opened to fill the inside of the supply pipe 4 and the inside of the flexible hose 8 with the residual hydrogen gas in the cylinder 7. Subsequently, the cylinder on-off valve 73 is closed to stop the filling, and gas is discharged by opening the discharge on-off valve 61. Thus, the inside of the supply pipe 4, the inside of the flexible hose 8, and the inside of the discharge pipe 6 are purged by using the residual hydrogen gas in the cylinder 7.

Next, in the state in which the cylinder on-off valve 73 and the discharge on-off valve 61 are closed, the pressure-reducing valve 43 is set at 5 MPa, and the inside of the supply pipe 4 and the inside of the flexible hose 8 are filled with hydrogen gas. Subsequently, the pressure-reducing valve 43 is set free (closed) to stop the filling, and the discharge on-off valve 61 is opened to discharge gas. Thus, the inside of the pipe from the hydrogen inlet 41 to the pressure-reducing valve 43, the inside of the supply pipe 4, the inside of the flexible hose 8, and the inside of the discharge pipe 6 are purged by using the hydrogen gas in the storage container (that is, hydrogen gas to be sampled).

In these steps, leak check of the supply pipe 4 and the flexible hose 8 may be performed by using the residual hydrogen gas in the cylinder 7 or the like.

After the discharge, the discharge on-off valve 61 is closed and the flow control valve 44 is opened to start filling from the storage container to take a sample of hydrogen gas into the cylinder 7. After the sample of hydrogen gas has been taken, the cylinder on-off valve 73 of the cylinder 7 is closed, the flow control valve 44 is closed, and the discharge on-off valve 61 is opened to discharge gas, and the flexible hose 8 is removed.

The cylinder unit 3 includes a temperature sensor (not shown) that measures the temperature of the cylinder 7. If the temperature becomes −10° C. or lower or 40° C. or higher while the cylinder 7 is being filled with hydrogen gas, the temperature sensor issues a warning.

In the embodiment described above, the pressure-reducing safety unit 2 includes the upper frame body 21a and the lower frame body 22a, the device accommodation chamber 21 is formed in the upper frame body 21a, and the cylinder connection chamber 22 is formed in the lower frame body 22a. However, the device accommodation chamber and the cylinder connection chamber may be disposed respectively on the left side and on the right side or may be disposed on the lower side and on the upper side in the opposite way.

In the embodiment described above, the pressure-reducing safety unit 2 and the cylinder unit 3 each have four wheels. However, the wheels of both units may be omitted, or only one of the units may have wheels.

What is claimed is:

1. A sampling apparatus comprising a pressure-reducing safety unit and a cylinder unit for taking a sample of hydrogen gas to a cylinder from a storage container of fuel hydrogen gas to be supplied to a hydrogen vehicle,
    wherein the pressure-reducing safety unit includes a device accommodation chamber that accommodates devices and a cylinder connection chamber in which a flexible hose for sampling is connectable to the cylinder,
    wherein the device accommodation chamber accommodates a supply pipe that introduces high-pressure hydrogen gas from the storage container, a safety pipe that discharges hydrogen gas in the supply pipe when a pressure of the hydrogen gas exceeds a set pressure, and a discharge pipe that discharges gas in a pipe extending from the supply pipe to the cylinder,
    wherein a hydrogen inlet from the storage container is disposed at one end of the supply pipe, a hydrogen outlet to the cylinder is disposed at the other end of the supply pipe, and the hydrogen outlet is located near a boundary between the device accommodation chamber and the cylinder connection chamber,
    wherein a pressure-reducing valve that reduces a pressure of the high-pressure hydrogen gas introduced from the hydrogen inlet and a flow control valve that adjusts a flow rate of the hydrogen gas whose pressure has been reduced by the pressure-reducing valve are disposed in the supply pipe,
    wherein the safety pipe and the discharge pipe, in which a discharge on-off valve is disposed, branch from a branching portion of the supply pipe between the pressure-reducing valve and the flow control valve,
    wherein a main valve, a rupture disk that opens the safety pipe at a first set pressure or higher, and a safety valve that opens at a second set pressure lower than the first set pressure and closes at a third set pressure lower than the second set pressure are disposed in the safety pipe in order from the branching portion of the supply pipe,
    wherein the cylinder connection chamber includes an open surface portion that opens toward the outside,
    wherein the cylinder unit removably accommodates the cylinder, excluding an exposed portion where a front end portion of the cylinder, a mouthpiece, and a cylinder on-off valve are exposed, in a casing, and
    wherein the exposed portion of the cylinder is formed so as to be insertable from the open surface portion of the cylinder connection chamber into the cylinder connection chamber, and the sample of hydrogen gas is taken into the cylinder by connecting the mouthpiece of the cylinder and the hydrogen outlet by using the flexible hose.

2. The sampling apparatus according to claim 1, wherein the pressure-reducing safety unit includes four wheels at a bottom portion of the unit and is portable, and the cylinder unit includes four wheels at a bottom portion of the unit and is portable.

3. The sampling apparatus according to claim 2,
    wherein the cylinder unit includes a rotatable frame including an angular C-shaped frame body including a pair of frame members that are parallel to a longitudinal direction of the cylinder and a first handle that connects one end portions of the pair of frame members, a pair of wheels disposed at end portions of the frame body, a connection member that connects portions of the frame body near end portions, and a rotatable arm one end of which is attached so as to be rotatable with a center of the connection member as a fulcrum and the other end of which is attached so as to be rotatable with a center of a bottom frame of the cylinder unit in the longitudinal direction as a fulcrum, a rotatable frame allowing positions of the pair of wheels disposed on the frame body to be variable,
    wherein the bottom frame includes a first engagement portion and a second engagement portion that engage with the first handle when the rotatable frame is rotated,
    wherein, when the rotatable frame is rotated and the first handle engages with the first engagement portion, the pair of wheels, whose positions are variable, are located near the other pair of wheels near a bottom portion of the cylinder, and
    wherein, when the rotatable frame is rotated and the first handle engages with the second engagement portion, the rotatable arm and the angular C-shaped frame body form a predetermined angle and one of the pairs of wheels and the other pair of wheels are positioned on the same plane so as to be separated by a predetermined distance and the cylinder unit is in an inclined state.

4. The sampling apparatus according to claim 1, wherein the casing of the cylinder unit has a horizontally-elongated rectangular-parallelepiped shape and includes a pair of openable/closable casings formed by dividing an upper surface at a center in a longitudinal direction, each of the pair of openable/closable casings including a side surface and a divided upper surface and having an L-shaped vertical cross section perpendicular to the longitudinal direction; and a plurality of hinges are disposed at a lower end of the side surface of each of the pair of openable/closable casings and a grip for opening/closing is disposed on the divided upper surface of each of the pair of openable/closable casings, so that the pair of openable/closable casings are openable/closable.

5. A sampling method for taking a sample of hydrogen gas to a cylinder from a storage container of fuel hydrogen gas to be supplied to a hydrogen vehicle by using a sampling apparatus including a pressure-reducing safety unit and a cylinder unit, wherein the pressure-reducing safety unit includes a device accommodation chamber that accommodates devices and a cylinder connection chamber in which a flexible hose for sampling is connectable to the cylinder, wherein the device accommodation chamber accommodates a supply pipe that introduces high-pressure hydrogen gas from the storage container, a safety pipe that discharges hydrogen gas in the supply pipe when a pressure of the hydrogen gas exceeds a set pressure, and a discharge pipe that discharges gas in a pipe extending from the supply pipe to the cylinder, wherein a hydrogen inlet from the storage container is disposed at one end of the supply pipe, a hydrogen outlet to the cylinder is disposed at the other end of the supply pipe, and the hydrogen outlet is located near a boundary between the device accommodation chamber and the cylinder connection chamber, wherein a pressure-reducing valve that reduces a pressure of the high-pressure hydrogen gas introduced from the hydrogen inlet and a flow control valve that adjusts a flow rate of the hydrogen gas whose pressure has been reduced by the pressure-reducing valve are disposed in the supply pipe, wherein the safety pipe and the discharge pipe, in which a discharge on-off valve is disposed, branch from a branching portion of the supply pipe between the pressure-reducing valve and the flow control valve, wherein a main valve, a rupture disk that opens the safety pipe at a first set pressure or higher, and a safety valve that opens at a second set pressure lower than the first set pressure and closes at a third set pressure lower than the second set pressure are disposed in the safety pipe in order from the branching portion of the supply pipe, wherein the cylinder connection chamber includes an open surface portion that opens toward the outside, and wherein the cylinder unit removably accommodates the cylinder, excluding an exposed portion where a front end portion of the cylinder, a mouthpiece, and a cylinder on-off valve are exposed, in an openable/closable casing, the sampling method comprising:

inserting the exposed portion of the cylinder into the cylinder connection chamber from the open surface portion of the cylinder connection chamber, connecting the mouthpiece of the cylinder and the hydrogen outlet by using the flexible hose, and connecting the hydrogen inlet to a filling hole of the storage container;

filling an inside of the supply pipe and an inside of the flexible hose with residual hydrogen gas in the cylinder by opening the cylinder on-off valve and the flow control valve, subsequently stopping the filling by closing the cylinder on-off valve, and discharging gas by opening a discharge on-off valve; and starting filling an inside of the cylinder from the storage container by closing the discharge on-off valve and opening the cylinder on-off valve to take the sample of hydrogen gas into the cylinder.

* * * * *